(12) United States Patent
Zaru et al.

(10) Patent No.: US 8,778,367 B2
(45) Date of Patent: Jul. 15, 2014

(54) GLYCEROSOMES AND USE THEREOF IN PHARMACEUTICAL AND COSMETIC PREPARATIONS FOR TOPICAL APPLICATIONS

(75) Inventors: Marco Zaru, Monza (IT); Maria Letizia Manca, Monza (IT); Anna Maria Fadda, Monza (IT); Gaetano Orsini, Monza (IT)

(73) Assignee: Prigen S.R.L., Monza (IT)

(*) Notice: Subject to any disclaimer, the term of this patent is extended or adjusted under 35 U.S.C. 154(b) by 0 days.

(21) Appl. No.: 13/255,144

(22) PCT Filed: Mar. 8, 2010

(86) PCT No.: PCT/EP2010/001428
§ 371 (c)(1),
(2), (4) Date: Nov. 4, 2011

(87) PCT Pub. No.: WO2010/102770
PCT Pub. Date: Sep. 16, 2010

(65) Prior Publication Data
US 2012/0141565 A1 Jun. 7, 2012

(30) Foreign Application Priority Data
Mar. 10, 2009 (IT) ............................. MI2009A0350

(51) Int. Cl.
| | | |
|---|---|---|
| *A61K 8/02* | (2006.01) | |
| *A61K 9/127* | (2006.01) | |
| *A61K 8/00* | (2006.01) | |
| *A61K 8/18* | (2006.01) | |
| *A61Q 17/04* | (2006.01) | |
| *A61Q 5/00* | (2006.01) | |
| *A61Q 9/00* | (2006.01) | |
| *A01N 43/90* | (2006.01) | |
| *A61K 31/522* | (2006.01) | |

(52) U.S. Cl.
USPC ............ 424/401; 424/450; 424/59; 424/70.1; 514/263.38

(58) Field of Classification Search
CPC ........................................................ A61K 9/127
USPC ............... 424/401, 450, 59, 70.1; 524/263.38
See application file for complete search history.

(56) References Cited

U.S. PATENT DOCUMENTS

| | | | |
|---|---|---|---|
| 6,117,857 A | * | 9/2000 | Carlsson et al. ............... 514/129 |
| 6,348,215 B1 | * | 2/2002 | Straubinger et al. ........... 424/450 |
| 2006/0099244 A1 | | 5/2006 | Guilford |
| 2009/0232881 A1 | * | 9/2009 | Bandyopadhyay et al. .. 424/450 |
| 2009/0324709 A1 | * | 12/2009 | Moscoso Del Prado et al. ............................ 424/450 |

FOREIGN PATENT DOCUMENTS

| | | |
|---|---|---|
| EP | 1 013 268 A1 | 6/2000 |
| EP | 1987813 A1 * | 11/2008 |
| WO | 92/18103 A1 | 10/1992 |
| WO | WO 2006103091 A1 * | 10/2006 |

OTHER PUBLICATIONS

Notification of Transmittal of the International Search Report and the Written Opinion of Th Einternational Searchign Authority, or the Declaration, mailed data Jun. 9, 2010.

* cited by examiner

*Primary Examiner* — Robert T Crow
*Assistant Examiner* — Doan Phan
(74) *Attorney, Agent, or Firm* — Silvia Salvadori, P.C.

(57) ABSTRACT

The present invention relates to vesicles for topical delivery of drugs and cosmetics, named glyceromes and characterized by high content of glycerol. The invention further relates to pharmaceutical formulations and cosmetic products containing glycerosomes.

13 Claims, 5 Drawing Sheets

GLYCEROSOMES AND USE THEREOF IN PHARMACEUTICAL AND COSMETIC PREPARATIONS FOR TOPICAL APPLICATIONS

This application is a U.S. national stage of PCT/EP2010/001428 filed on Mar. 8, 2010 which claims priority to and the benefit of Italian Application No. MI2009A000350 filed on Mar. 10, 2009, the contents of which are incorporated herein by reference.

The present invention relates to vesicular nanostructures useful for the formulation of active pharmaceutical ingredients and cosmetic products and to their application for topical delivery of drugs and cosmetics. The vesicular nanostructures described in the present invention are named glyceromes due to the their high content of glycerol.

BACKGROUND OF THE INVENTION

Topical drug delivery, compared to conventional routes of administration such as oral or parenteral delivery, is both potentially advantageous since it avoids active principle degradation in gastrointestinal tract and first pass hepatic metabolism and it is more acceptable by patients.

However the skin, which consists of two layers, the deeper one or dermis and the external layer or epidermis, behaves as a difficult to permeate barrier for most drug substances.

The deeper layer or dermis, whose thickness is between 0.3 and 4 mm, consists of connective tissue embedded with blood vessels, pilo-sebaceous units (hair follicles and sebaceous glands) as well as nerve endings which makes skin a true sense organ. At dermis level, active principles can cross the capillary walls to enter into the circulatory system and reach different tissues. The outermost layer of the skin or epidermis, whose thickness is between 50 and 150 µm, is covered by a hydrolipidic film and performs a barrier function against microorganisms and other exogenous molecules from the surrounding environment. Keratinocytes are the typical epidermis cells that originate at the innermost layer close to dermis and undergo a gradual differentiation process called keratinization ending with migration to surface to form a horny layer of dead cells (statum corneum) with thickness between 10 and 30 µm.

The horny layer acts as an effective barrier limiting the passage of active principles whose rate of transdermal absorption correlates with the generally very low rate of their penetration through the horny layer. Due to this barrier effect, the topical administration of drugs normally results in a reduced bioavailability.

Different approaches have been investigated to improve the diffusion of drugs through the skin including physicochemical methods based on the use of penetration enhancers such as dimethylsulphoxide, fatty acids, propylene glycol and urea [Williams A C e Barry B W, 1992] as well physical methods including, among others, iontophoresis, electroporation and low-frequency ultrasound [Lavon I e Kost J, 2004] or a combined application of both physical methods and chemical enhancers.

A different approach to improve the transdermal diffusion of drugs is based on the carrier properties of vesicular structures generally indicated as liposomes. Liposomes are microscopic vesicles of 50-500 nm containing amphiphatic phospholipids which are molecules that have a polar head and a lipidic tail. In aqueous environment the hydrophilic heads line up to form a surface facing the water while the hydrophobic tails, repelled by water, line up to form a surface away from the water; moreover, the hydrophobic tails of one layer interact with the hydrophobic tails of another layer to form closed bilayer structures organized as uni-lamellar or multi-lamellar vesicles containing one or more aqueous compartments.

The chemicophysical properties of liposomes can be easily modified by variations of preparation methods and/or by including in their composition different substances such as, for example, cholesterol which increases the stability of lipidic bilayer, or acidic or basic lipid molecules which modify the electrical charge of vesicular surfaces and reduce liposome aggregation.

Hydrophilic compounds are solubilized in liposomes aqueous compartments and hydrophobic compounds enter into the lipidic bilayers while amphipathic molecules are distributed with their polar portions in water and apolar portions in lipidic lamellae Moreover, ingredients used to prepare liposomes are safe, non allergenic and being fully compatible with biological membranes enable the interaction of liposomes with cells.

Different mechanisms have been suggested to explain the interaction between liposomes and cells and some of them can possibly occur together. The most plausible mechanism is endocytosis where intact liposomes are phagocytated by cells and internalized into lysosomes where the drugs are released by phospholipase degradation of lipidic bilayers. Other putative mechanisms are based on lipidic substance exchange due to fusion of liposome bilayers with cell membranes followed by distribution of vesicle content between cytoplasmic compartment and cell membranes in dependence of its physicochemical properties.

The use of liposomes for targeted drug delivery at dermis and epidermis level with the aim to reduce systemic absorption and undesired effects has been first suggested in 1980 [Mezei M e Gulasekharam V, 1980; Mezei M, 1988] and then studied by many authors [Lichtenberg D e Barenholz Y, 1988; Woodle M C e Papandjopoulos D, 1989, Sinico C et. al 2005, Manconi M et. Al 2006]. In some cases, liposomes can be used for transdermal permeation of drugs or cosmetic agents through skin appendages, such as hair follicles and sebaceous glands since, at this level, in dependence of liposome composition and preparation technique, active principles can cross the capillary walls and reach different tissues and organs from blood circulation [El Maghraby G. M et al., 2006]. In most cases, however, the use of liposomes as carriers for topical and/or transdermal administration of active principles is of little or no value since conventional liposomes do not penetrate the skin but rather remain confined to the upper layers of the stratum corneum. Later on, new classes of lipidic vesicles have been developed, namely deformable lipid vesicles and ethosomes, where the presence of specific additives modify the chemicophysical and functional properties of conventional liposomes enabling a more efficient delivery of drugs to deeper layers of the skin.

Deformable or flexible liposomes (also called Transferomes®) incorporate, besides the basal phospholipidic component, single chain surfactants with a high radius of curvature (selected, for example, among sodium cholate, sodium deoxycholate, potassium glycyrrhizinate, Span® 60 sorbitane monostearate, Span® 65 sorbinate tristearate, Span® 80 sorbitane monooleate, Tween® 20 polyethylene glycol sorbitan monolaureate, Tween® 60 polyethylene glycol sorbitan monostearate, Tween® 80 polyethylene glycol sorbitan monooleate) which are able to destabilizes vesicle lipidic bilayers and increase liposome deformability given them a higher skin penetration capability [Cevc G, Blume G, 1992].

Transferosomes are morphologically similar to standard liposomes even if they are functionally different being sufficiently deformable and flexible to penetrate pores much smaller than their own size. The mechanism of action of transferosomes is based both on a better capability of intact deformable vesicles to enter the stratum corneum and on subsequent modification and destabilization of intercellular lipidic structures which facilitate the diffusion of free drug molecules from the vesicles.

However, since the transport mechanisms of these deformable vesicles could partially depend on the physicochemical properties of incorporated drugs, the preparation of transferosomes need to be optimized on a case-by-case basis [El-sayed M M A et al., 2006].

A different approach to increase the fluidity of lipidic membranes of liposomes in order to improve their function as carriers of drugs and/or cosmetic products is represented by lipid vesicles called ethosomes composed of phospholipids, water and high concentrations, generally between 20% and 50%, of ethanol [Touitou E, U.S. Pat. No. 5,716,638]. High ethanol concentrations reduce the ethosomes size and, in general, increase their encapsulation efficiency for a wide range of active principles including lipophilic molecules resulting in an effective delivery system for topical administration of drugs [Touitou E at al., 2000].

The action of ethosomes is possibly due to a synergistic mechanism between ethanol, lipid vesicles and skin lipids where the presence of ethanol could provide the vesicles with flexible characteristics for a better penetration into deeper layers of the skin as well as display its well-known permeation enhancing effect [Williams A, 2003].

Besides, ethosomes penetrated into the deep layers of the skin could fuse with skin lipids promoting the release of drugs at dermis level and possibly their transdermal absorption.

However, because of the high content of ethanol, the use of ethosomes as delivery system for drugs and/or cosmetic products may have unfavourable or irritating effects in case of application on wounded or otherwise injured skin.

DESCRIPTION OF THE INVENTION

During the development of liposome-like formulations, the inventors have surprisingly found new vesicle structures with improved carrier characteristics for use in the pharmaceutical and cosmetic fields. These new formulations, called glycerosomes, are composed by phospholipids and water and are characterized by containing a high amount of glycerol (from 20 to 35%) which, unlike ethanol contained in ethosomes, is a harmless and fully accepted compound for topical applications. Additionally, unlike the liposomes known in the art [as for example in Fukui M, EP 1013268; Guilford F T, US 2006/0099244 and in Leigh S, WO 92/18103], the glycerosomes of the present invention are specifically characterized by being prepared in the absence of ethanol in order to avoid its irritating action following topical application.

Glycerosomes according to the invention, whose glycerol content is between 20% and 35% w/w, preferably from 20% to 30%, more preferably 25%, can be prepared from any natural or synthetic phospholipids commonly used in the preparation of conventional liposomes known in the art; similarly, glycerosomes can contain one or more additives commonly used in the preparation of conventional liposomes known in the art and can be obtained by any of the different techniques commonly used for the preparation of conventional liposomes known in the art, e.g. according to the methods described in the following publications and patents herein incorporated by reference: Vemuri S, Rhodes C T. 1995; Cevc G. 2004; Torchilin V P, Weissig V, 2003.

In a further embodiment of the invention, glycerosomes can be used as carriers of active principles and incorporated in formulations for topical applications known in the art comprising, but not limited to, creams, emulsions, ointments, gels, lotions, suspensions and equivalent formulations.

Exemplary compositions of glycerosomes according to the present invention are reported in the following table 1:

| Phospholipids | Glycerol | Modifiers | Absorption Enhancers | Active principles | Preservatives | Water |
|---|---|---|---|---|---|---|
| 1-10% | 20-35% | 0-2% | 0-5% | 0-20% | 0-1% | to 100% |

The phospholipid components consist of one or more phospholipids extracted by natural sources or of phospholipids prepared by synthetic or semi-synthetic methods such as, for example, phosphatidylcholine (lecithin), phosphatidylethanolamine, phosphatidylserine, phosphatidylglycerol, phosphatidylinositol, dimiristoylphosphatidylcholine (DMPC), dipalmitoyl phosphatidylcholine (DPPC), distearoyl phosphatidylcholine, palmitoyl-stearoyl phosphatidylcholine, sphingomyelin, mixtures of soybean derived hydrogenated and non hydrogenated phospholipids such as Phospholipon® 90 (p90) lecithin, Phospholipon 100 (p100) polyene phosphatidylcholine, Phospholipon® 90G (p90G) phosphatidylcholine, Phospholipon® 90H (p90H) hydrogenated phosphatidylcholine as well as similar mixtures. The most relevant properties that the phospholipids should possess to be used in the preparation of glycerosomes according to the invention are (i) capability to give vesicles which are able to incorporate the active principles, (ii) biological compatibility, (iii) metabolic degradation and (iv) lack of toxicity.

The modifier components, added to glycerosomes as stabilizers and/or to modify their electric charge may be selected from cholesterol, stearylamine and dicetylphosphate.

The absorption enhancers can be selected from dimethylsulphoxide, propylene glycol and fatty acids.

The glycerosomes of the present invention can be prepared according to different approaches known in the art for preparing conventional liposomes including, for example, the method of lipidic film hydration first described by Bangham et al (1965) as well as methods based on the same principles [Kirby C e Gregoriadis G, 1984]; the reverse-phase evaporation techniques [Skoza F, Papahadjopoulos D, 1980; Papahadjopoulos D et al., U.S. Pat. No. 4,235,871; Pick U, 1981]; the method of supercritical reverse-phase evaporation [Imura T et al., 2002].

Depending on composition and method of preparation, the glycerosomes of the present invention can results in unilamellar lipidic vesicles (small or large) or in multilamellar lipid vesicles. Glycerosomes in form of multilamellar vesicles can be converted in unilamellar vesicles by sonication or homogenization, by extrusion or by filtration through membranes with a specific pore size.

It is worth noting that glycerosomes containing more than 20% w/w glycerol are more effective than those having lower glycerol (for example from 10 to 15%) in several respects:

a) A higher glycerol (>20%) concentration improve the rheological properties (e.g. viscosity) and, consequently, give a positive contribute to the stabilization of the glycerosome vesicular system.

b) A glycerol concentration lower than 20% hamper the assembling of vesicles at room temperature (namely at 25° C.) when phospholipids with high transition temperatures (e.g. 70-80° C.) were used for preparing glycerosomes.

c) Vesicles prepared with a low glycerol concentration (10-15%) display a reduced flexibility and possibly a reduced skin permeation capacity.

Glycerosomes of the present invention can be used as carriers to deliver active principles of pharmaceutical or cosmetic interest including, but not limited to, lipophilic compounds such as acyclovir, trans-retinoic acid, betamethasone dipropionate, lidocain, minoxidil, amphotericin B, gentamycine, rifampicin, vitamin E and esters or lipophilic derivatives of vitamin E, etc. as well as hydrophilic compounds such as, for examples, diclofenac sodium, lidocaine hydrochloride, hyaluronic acid, vitamin C and its derivatives, soluble derivatives of vitamin E as vitamin E TPGS, etc.

To further illustrate the present invention, without limiting the field of application thereof, we have compared the chemicophysical and functional characteristics of glycerosomes with conventional liposomes—both prepared as described in Example 1—as carriers for antiviral drug acyclovir, for highly lipophilic synthetic steroidal compound betamethasone dipropionate and for d-alpha-tocopheryl polyethylene glycol-1000 succinate (Vitamin E TPGS or Tocophersolan) which is a water soluble form of natural vitamin E used in pharmaceutical field and as antioxidant in cosmetic preparations.

Acyclovir is a acyclic purine nucleoside analogue used for topical treatment of recurrent orofacial lesions, particularly in cases of herpes labialis, which are caused by type 1 Herpes simplex virus (HSV-1) infections; an acyclovir formulation for topical treatment is commercially available as a cream containing 5% of active principle under the brand name Zovirax®.

As shown in table 2, carrier vesicles containing the phospholipid dipalmitoylphosphatidylcholine (DPPC) and the modifier agent cholesterol were loaded with two concentrations of active principle, namely 5% acyclovir in preparations A and 1% acyclovir in preparations B.

TABLE 2

Percent composition of glycerosomes and liposomes loaded with acyclovir.

| | DPPC | Cholesterol | Acyclovir | Glycerol |
|---|---|---|---|---|
| Glycerosomes-A | 3 | 0.1 | 5 | 25 |
| Glycerosomes-B | 3 | 0.1 | 1 | 25 |
| Liposomes-A | 3 | 0.1 | 5 | — |
| Liposomes-B | 3 | 0.1 | 1 | — |

The efficiency of active principle entrapment is calculated taking into consideration the amount non incorporated and separated during glycerosomes purification on a gel filtration column. In fact, the amount of active principle incorporated into purified glycerosome preparations is measured after disruption of purified vesicles by action of Triton™ X100 octylphenol ethyxylate or methanol. The efficiency of incorporation (E %) is then expressed as percentage of active principle taken up by vesicles with respect to the initial loading amount, according to the following equation:

$$E\% = \text{amount of active principle of purified preparation} \times 100 / \text{initial load of active principle}$$

Glyceromes showed a significantly higher incorporation efficiency of acyclovir with respect to the incorporation in conventional liposomes, as reported in table 3.

TABLE 3

Incorporation efficiency of acyclovir in glycerosomes and liposomes. Incorporation efficiency of acyclovir (%)

| Glycerosomes-A | Liposomes-A |
|---|---|
| 54.4 ± 8 | 30.6 ± 5 |

A further advantage of glycerosomes is represented by the fact that they are prepared at room temperature, more preferably at temperature lower than 30° C. or, in a preferred embodiment at 25° C., irrespective of the type of phospholipid used for the preparation; on the contrary the operational temperature for preparing conventional liposomes corresponds to or is higher than the transition temperature (Tc) of phospholipidic components which, in some cases, can be in the range of 60-80° C., as for example with DPPC with a Tc=70° C. Avoiding any heating of the glycerosomes preparation mixtures represents an obvious advantage when the incorporated active principle is thermolable or can be partially decomposed upon heating.

Figure 1:
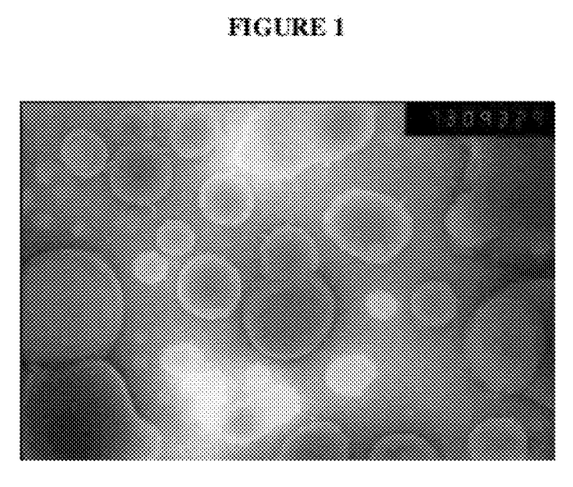
FIG. 1: Imaging of 5% acyclovir loaded glycerosomes by transmission electronic microscopy (TEM) analysis.

Morphological analyses of acyclovir loaded glycerosomes by optical microscopy in polarized light enabled the identification of maltese crosses which confirm the presence of lamellar systems assimilable to vesicular structures [Manosroi A et al., 2003; Mele S et al., 2003; Sinico C et al 2005]. The presence of lamellar vesicular structures was confirmed by transmission electronic microscopy (TEM) analysis of glycerosome preparations, as shown in FIG. 1.

The stability of preparations was studied by dimensional analysis according to the Photon Correlation Spectroscopy technique, by Z potential determination, by Dynamic Laser Light Scattering and by measuring the polidispersity index at various time (up to 3 weeks) following vesicles preparation.

Figure 2:
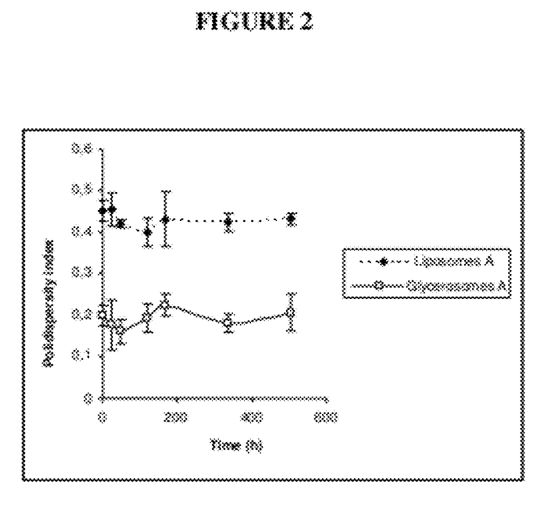
FIG. 2: Polidispersity index (PI) of 5% acyclovir loaded glycerosomes-A and liposomes-A measured at various time following vesicles preparation.

Average size of glycerosomes and liposomes (as calculated in triple on three different preparations) were respectively around 100 nm and 150 nm, while the calculation of polidispersity index (PI), which represents an important parameter to evaluate the homogeneity of vesicular preparations, demonstrated higher homogeneity for glycerosomes with average PI values of 0.2 in comparison to average PI value of 0.4 for liposomes, as shown in FIG. 2. The better homogeneity of glycerosomes is a particularly useful property for their use in delivery systems of pharmaceutical and cosmetic interest.

Besides, the high content of glycerol resulted in a higher glycerosomes flexibility in comparison to conventional liposomes, as demonstrated by measuring the mean particle size and the polydispersity index before and after extrusion of the preparations through 50 nm pore size filters, as shown in table 4.

TABLE 4

Extrusion test of 5% acyclovir loaded glicerosomes and liposomes on 50 nm pore size filters.

|  | Before extrusion | | After extrusion | |
| --- | --- | --- | --- | --- |
|  | Size nm ± SD | PI | Size nm ± SD | PI |
| Glycerosomes-A | 108 ± 33 | 0.23 | 105 ± 24 | 0.27 |
| Liposomes-A | 148 ± 28 | 0.45 | 98 ± 21 | 0.63 |

The results of table 4 clearly show the higher stiffness of conventional liposomes which after extrusion showed a significant size reduction while polidispersity index increased due to the fact that only the vesicles whose size were comparable to the membrane porosity were filtered intact while larger vesicles were damaged and partially disrupted.

The higher glycerosomes flexibility represents a further useful property for their application as carriers for topical drug delivery since the use of more flexible vesicles can potentiate the penetration and transport of active principles into deep skin layers [Cevc G, Gebauer D., 2003].

Transdermal absorption from 5% acyclovir loaded glycerosomes and liposomes, that is the releasing and permeation of active principle through the skin, was assessed in a vertical Franz cell which is a suitable experimental approach to study percutaneous absorption of topical formulations using a membrane from newborn pig skin. As described in example 6, the cell was maintained in a thermostatic bath at skin physiological temperature of 32° C. up to 24 hours; at the end of the experiment porcine skin specimen used in Franz cell as membranes were manually sectioned and stratum corneum, epidermis and dermis were separately analyze to measure the distribution of active principle in different skin layers.

Figure 3:
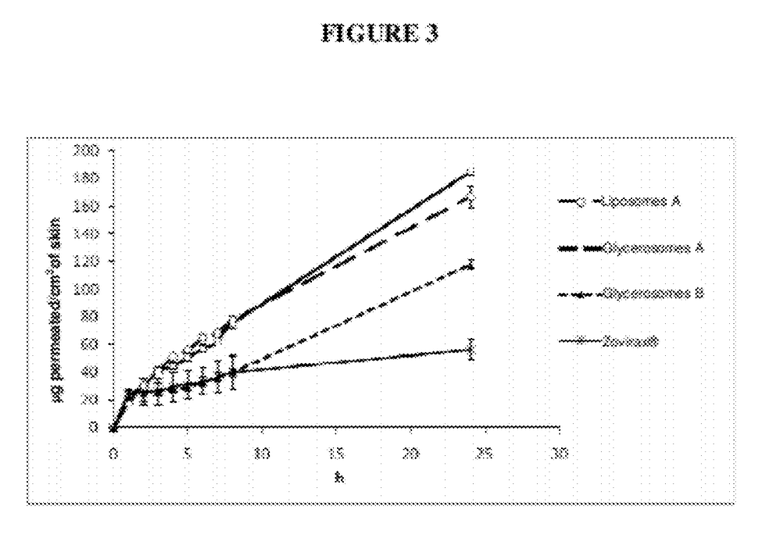
FIG. 3: Permeation profiles of 5% acyclovir loaded glycerosomes-A, glycerosomes-B and liposomes in comparison to a commercial 5% acyclovir cream (Zovirax®). The experiments have been performed for 24 hours, in Franz cells equipped with separation membranes (0.636 cm$^2$) from newborn pig skin maintained at the physiological temperature of 32° C.

In these experiments, 5% acyclovir loaded glycerosomes and liposomes were compared to a commercially available acyclovir cream for topical applications (Zovirax®, 5% acyclovir cream) and the results in terms of time dependent acyclovir permeation and acyclovir distribution in different skin layers are respectively shown in FIG. 3 and table 5.

According to the results of FIG. 3, 5% acyclovir loaded glycerosomes-B containing 25% glycerol showed a higher in vitro permeation flow (measured as µg acyclovir/cm² skin) when compared to both conventional liposome formulations and commercial 5% acyclovir cream. In particular, acyclovir permeation in 24 hours from glycerosomes was about 4 fold higher than permeation from commercial cream formulation. The results of FIG. 3, showing that 1% acyclovir loaded glycerosomes-B gave a total permeation flow still 2 fold higher in comparison to commercial cream formulation can be considered a potential advantage in terms of safety enabling to use lower dosages and from economical/productive point of views enabling to reduce the amount of active principle.

The distribution of acyclovir among different cutaneous compartments after 24 hour permeation, as showed in table 5, demonstrate higher epidermis accumulation in the case of vesicular formulations while in the case of commercial cream the major amount of active principle was confined in stratum corneum. Even if accumulation at dermis and epidermis level did not show statistically significant differences among different formulations, the results of table 5 confirm differences in flow rates and strengthen the penetration enhancer capability of glycerosomes.

TABLE 5

Accumulation in different skin layers from 5% acyclovir loaded glycerosomes and liposomes in comparison to a commercial 5% acyclovir cream (Zovirax ®). The experiments have been performed for 24 hours, in a Franz cell equipped with a diffusion membrane (0.636 cm²) from newborn pig skin.

|  | Stratum corneum | | Epidermis | | Dermis | |
| --- | --- | --- | --- | --- | --- | --- |
|  | µg/g | Dose adsorbed % | µg/g | Dose adsorbed % | µg/g | Dose adsorbed % |
| Glycerosomes-A | 67 ± 4 | 0.27 ± 0.002 | 227 ± 13 | 0.91 ± 0.05 | 67 ± 4 | 0.27 ± 0.03 |
| Liposomes-A | 76 ± 9 | 0.30 ± 0.003 | 178 ± 35 | 0.71 ± 0.14 | 44 ± 13 | 0.18 ± 0.05 |
| Zovirax | 527 ± 35 | 2.10 ± 0.140 | 183 ± 71 | 0.73 ± 0.28 | 80 ± 17 | 0.32 ± 0.07 |

Betamethasone dipropionate is a lipophilic synthetic corticosteroid which as ointment, lotion or cream formulations is used for topical treatment of corticosteroid responsive dermatitis due to local anti-itching, anti-inflammatory and vasoconstrictive effects.

The incorporation efficiency of betamethasone dipropionate is higher for glycerosomes than for conventional liposomes which respectively showed an incorporation index value E % of 68% and 42%.

Figure 4:
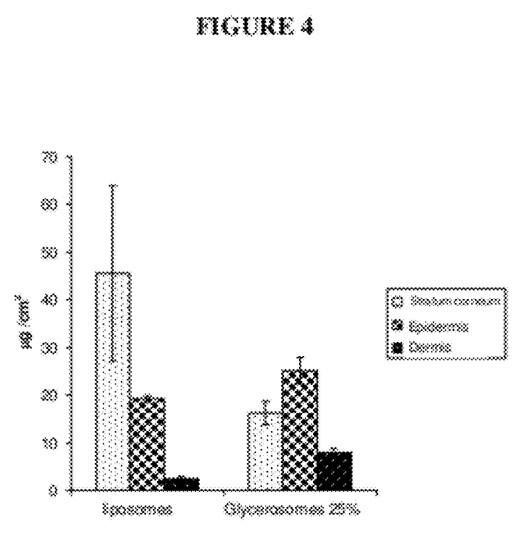
FIG. 4: Distribution of 0.2% betamethasone dipropionate loaded glycerosomes containing 25% glycerol and conventional liposomes, after 24 hour permeation in Franz cells equipped with separation membranes (0.636 cm$^2$) from newborn pig skin.

The distribution in different cutaneous compartments of 0.2% loaded glycerosomes-A containing 25% glycerol and conventional liposomes was studied in 24 hour diffusion experiments using newborn pig skin in Franz cells; the results shown in FIG. 4 demonstrate that glycerosomes loaded with a highly lipophilic compound as betamethasone dipropionate increased the accumulation of active principle in deep skin layers.

D-alpha-tocopheryl polyethylene glycol-1000 succinate (Vitamin E-TPGS or Tocophersolan) is a water soluble derivative of natural vitamin-E prepared by esterification of free carboxylic group of vitamin-E succinate with 1,000 Dalton polyethylene glycol. Vitamin E-TPGS can enter in pharmaceutical formulations as emulsifier, surfactant and absorption enhancer and can be used in cosmetic formulations and skin care products because of its antioxidant properties.

Due to its amphiphilic properties, vitamin E TPGS is entrapped into lipidic bilayers of liposomes.

Figure 5:
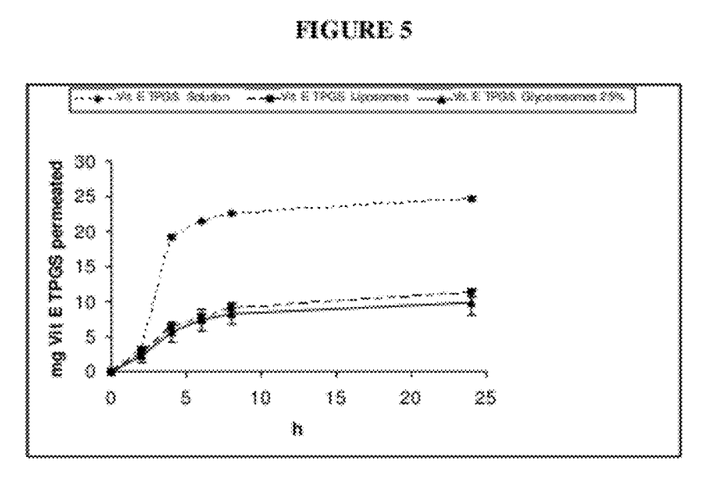
FIG. 5: Permeation profiles of 10% Vitamin E TPGS loaded glycerosomes-A containing 25% glycerol and conventional liposomes in comparison to Vitamin E TPGS aqueous solution. The experiments were performed for 24 hours in Franz cells equipped with separation membranes (0.636 cm$^2$) from newborn pig skin.

In vitro diffusion of 10% vitamin E TPGS loaded glycerosomes-A containing 25% glycerol and conventional liposomes was studied in Franz cells equipped with separation membranes from newborn pig skin and the results are shown in FIG. 5. Both formulations gave permeation profiles indicating a mechanism of controlled release as demonstrated by the low amount of 24 hour permeates (10-12 milligrams corresponding to about 5% of initially loaded product) and by the fact that, in the same experimental conditions, 20-22% of vitamin E TPGS permeated from an aqueous solution in a steep burst within the first 4 hours (FIG. 5).

In the same experiments, the analysis of Vitamin E TPGS content in different skin compartments, as shown in table 6, demonstrated a higher accumulation in deep skin layers (deep epidermis/dermis) starting from 10% Vitamin E TPGs loaded glycerosomes with respect both to conventional liposomes and water solution.

TABLE 6

Accumulation of Vitamin E TPGS in deep skin layers (deep epidermis/dermis)

| Formulations | Vitamin E TPGS mg/gr skin tissue |
|---|---|
| Water solutions | 1.05 ± 0.49 |
| Liposomes-A | 1.80 ± 0.42 |
| Glycerosomes-A | 3.09 ± 0.58 |

The relationships between permeation profiles and accumulation in different skin compartments demonstrate that vesicular structures function as a Vitamin E TPGS depot system; this effect is greater with Vitamin E TPGS loaded glycerosomes which give a larger accumulation in deep skin layers and a burst-free permeation profile.

The combination of burst effect during permeation and of minor skin accumulation observed in the case of Vitamin E TPGS water solutions can be considered as an indication of higher permeation capability and of likely systemic absorption.

In conclusion, the glycerosomes according to the present invention, in comparison to conventional liposomes and other conventional formulations for topical administration such as creams, lotions, ointments or solutions display better permeation profiles acting as fully biocompatible skin penetration enhancers and are therefore useful carriers for topical administration of pharmaceutical active principles and cosmetic products with high skin permeation capability and without risks of cutaneous irritation.

In fact, the glycerosomes described in the present invention, being characterized by a glycerol content between 20% and 35% do not contain any aggressive component, such as ethyl alcohol, which after topical application could cause irritation or burn in the presence of cutaneous lesion as in the case, for example, of herpes labialis or other types of skin damages.

Below, experimental examples are given with the purpose to illustrate some preferred embodiments, without limiting the field of application of the invention.

EXAMPLE NO 1

Preparation of Glycerosomes and Liposomes

Glyceromes and liposomes were prepared according to the lipidic film hydration technique. Briefly, weighted lipidic components (phospholipids, cholesterol, hydrophobic active principles or ionic lipids such as DCP or stearylamine) were dissolved in 5 ml of organic solvent (chloroform or dichloromethane) using a 50 ml round bottom flask containing 4-5 ml of 1 mm diameter glass beads. Solvent was removed using a rotary evaporator under vacuum at room temperature for 2 hours to get on the wall of the flask a lipidic film free of any trace of solvent. 5 ml of glycerol aqueous solution (glycerol concentration between 20% and 35%) also containing, if required, water soluble active principles were then added and the mixture was maintained under mechanical agitation at 10.000 rpm for 1 hour at 25° C. using a crescent-shaped plastic stirring shaft in close contact with the internal round bottom flask surface. The emulsion, consisting of multilamellar vesicles, was maintained at rest for 1 hour and then homogenized at high-pressure for 10 minutes at 25° C. using a Avestin Emulsiflex C5 homogenizer set at 60,000-65,000 kPa. Homogenated vesicles were purified by gel filtration on a Sephadex® G25 column, a bead-formed gel prepared by cross-linking dextran with epichlorohydrin, to separate glyceromes, which were eluted in void volume, from non incorporated active principle. Column elution was carried out with water and the collected fractions were checked by UV turbidimetric analysis at 600 nm to identify the vesicle rich fractions.

Conventional liposomes were prepared as described but performing lipidic film hydration with aqueous buffer (for example with saline phosphate buffer); besides, both hydration and next homogenization phases were carried out at a temperature corresponding to or higher than the transition temperature (Tc) of the phospholipidic component (for example DPPC with Tc=70° C.; DMPC with Tc=25° C.; etc).

EXAMPLE NO 2

Glycerosomes Characterization

Glycerosomes preparations were characterized by Transmission Electron Microscopy (TEM), optical microscopy in polarized light (PLM), Photon Correlation Spectroscopy (PCS) and by measurement of incorporation efficiency (E %).

For TEM, a drop of vesicular dispersion was applied to a copper grid, stained with 1% phosphotungstic acid solution and examined to confirm the vesicle formation as well as their morphology.

Vesicle dimensions and Z potential measurements were performed by a dynamic laser light scattering (DLLS) equipped with a Z-potential detector (Malvern).

For the calculation of E % values, corresponding to the fraction of drug incorporated into vesicles with respect to the initial loading (100%), loaded vesicles were separated from non incorporated drug by gel filtration on a column of Sephadex® G25 column, a bead-formed gel prepared by cross-linking dextran with epichlorohydrin, eluted with water.

EXAMPLE NO 3

Quantitative Analysis of Acyclovir

Acyclovir quantitative determinations were performed by UV spectrophotometry according to the method described in British Pharmacopeia. Briefly, acyclovir containing samples were completely dissolved in 0.5 M sulphuric acid an lipophilic components were extracted with ethyl acetate and analyzed at a wavelength of 254 nm in comparison to a calibration curve.

EXAMPLE NO 4

Preparation of Porcine Skin

In vitro permeation experiments were performed using newborn pig skin specimen obtained from local abattoirs, excised immediately after the animals' death, washed under running water, flatted on aluminum foils and stored at −20° C.

Newborn pig skin is thin, characterized by a regular thickness and free of fats under dermal layer.

EXAMPLE NO 5

Flexibility Assay

Vesicle flexibility was evaluated by an extrusion test consisting in the measurement of average dimensions and polidispersity index before and after vesicle filtration through a 50 nm pore size filtering membranes.

EXAMPLE NO 6

Permeation and Accumulation Studies

In vitro permeation studies were carried out in Franz diffusion cells under agitation with 500 µl vesicle samples loaded in upper cell compartment, or donor compartment. Specimen of frozen pig skin were rehydrated for 4 hours at room temperature in pH 7.4 phosphate buffer, cut in small discs and firmly secured between the two compartments of Franz cell by metal clamps. The available filtration surface of each disc was 0.636 cm$^2$. At consecutive time points during the experiments (0.5, 1, 2, 3, 4, 5, 6, 7, 8, and 24 hours) the content of lower compartment was completely withdrawn and replaced with fresh buffer avoiding the formation of air bubbles under the skin Collected samples were stored at 4° C. pending the determination of active principle content.

At the end of the experiments, skin discs were air-dried. The horny layer was pulled off by applying to skin, for 10 seconds, a Tesafilm adhesive tape (type 40021) under light pressure and repeating the stripping after 40° rotation of skin specimen. Dermis, separated from epidermis with a surgical scalpel, was then cut in small pieces and homogenized in buffer solution by sonication; the suspension was filtered and quantitative active principle analysis was performed on filtered solution.

Each experiment was carried out in triplicate in three parallel cells and repeated at least three times.

REFERENCES

Bangham et al. The action of steroids and streptolysin S on the permeability of phospholipid structures to cations. J. Mol. Biol. 13, 238-252, 1965.

Cevc G, Blume G. Lipid vesicles penetrate into intact skin owing to the transdermal osmotic gradients and hydration force. Biochim. Biophys. Acta 1104, 226-232, 1992.

Cevc G, Gebauer D. Hydration-driven transport of deformable lipid vesicles through fine pores and skin barrier. Biophys. J. 84, 1010-1024, 2003.

Cevc G. Lipid vesicles and other colloids as drug carrier on the skin. Adv. Drug Deliv. Rev. 56, 675-711, 2004.

El Maghraby G. M et al. Can drug bearing liposomes penetrate intact skin? J. Pharm. Pharmacol. 58, 415-429, 2006.

Elsayed M M A et al. Deformable liposomes and ethosomes: Mechanism of enhanced skin delivery. International Journal of Pharmaceutics 322, 60-66, 2006.

Fukui M. Compositions containing liposomes and/or emulsions and process for the preparation thereof. EP 1013268.

Guilford F T. Liposomal formulation for oral administration of glutathione (reduced). US Patent 2006/0099244.

Imura T et. al. Preparation and physicochemical properties of various soybean lecithin liposomes using supercritical reverse phase evaporation method. Colloids and Surface B: Biointerfaces. 27, 133-140, 2002.

Kirby C, Gregoriadis G. Dehydration-rehydration vesicles (DRV): A new method for high yield drug entrapment in liposomes. Biotechnology 11, 979-984, 1984.

Lavon I, Kost J. Ultrasound and transdermal drug delivery. Drug Discov. Today 9, 670-676, 2004.

Leigh S. Method for the formation of liposomes and compositions for use therein. WO 9218193.

Lichtenberg D, Barenholz Y. Liposomes: preparation, characterization and preservation. Meth. Biochem. Anal. 33, 337-461, 1988.

Manosroi A et al. Characterization of vesicles prepared with various non ionic surfactants mixed with cholesterol. Colloids and Surface B: Biointerfaces 30, 129-138, 2003.

Mele S et al. Monolein based liquid crystals to form long-term stable emulsion. Colloids and Surface A Physicochem Eng. Aspects 228, 57-63, 2003.

Mezei M, Gulasekharam V. Liposomes—a selective drug delivery system for topical route of administration. 1. Lotion dosage form. Pharm. Sci. 82 (1), 17-21, 1980.

Mezei M. Liposomes in topical application of drugs. Liposomes as Drugs Carriers: Recent Trends and Progress. Wiley J. & Sons, New York. Pag. 663-677, 1988.

Papahadjopoulos D et al. Methods of encapsulating biologically active material in lipid vesicles. U.S. Pat. No. 4,235,871.

Pick U. Liposomes with a large trapping capacity prepared by freezing and thawing of sonicated phospholipid mixtures. Arch. Biochem. Biophys. 212, 186-194, 1981.

Sinico C. et al. Liposomal incorporation of Artemisia Arborescens L. essential oil and in vitro antiviral activity. Eur. J. Pharm. Biopharm. 59, 161-168, 2005.

Sinico C et. al. Liposomes as carriers for dermal delivery of tretinoin: in vitro evaluation of drug permeation and vesicles skin interaction. J. Contr. Rel 103, 123-126, 2005.

Manconi et. al. Niosomes as carriers for tretinoin III. A study into in vitro cutaneous delivery of vesicles-incorporated tretinoin. Int. J. Pharm. 311, 11-19, 2006.

Skoza F, Papahadjopoulos D. Comparative properties and methods of preparation of lipid vesicles (liposomes). Annu. Rev. Biophys. Bioeng. 9, 467-508, 1980.

Torchilin V P, Weissig V (editors). Liposomes. Practical approach. Oxford University Press, Oxford, 2003.

Touitou E. Composition for applying active substances to or through the skin. U.S. Pat. No. 5,716,638.

Touitou E et al. Ethosomes—novel vesicular carriers for enhanced delivery: characterization and skin penetration properties. J. Control. Rel. 65, 403-418, 2000.

Vemuri S, Rhodes C T. Preparation and characterization of liposomes as therapeutic delivery systems: a review. Pharm. Acta Helv. 70, 95-111, 1995.

Williams A C, Barry B W. Skin absorption enhancers. Crit. Rev. Ther. Drug Carr. Sys. 9, 305-53, 1992.

Williams A. Transdermal and Topical Drug Delivery, 1st ed. Pharmaceutical Press, London, 2003.

Woodle M C, Papandjopoulos D. Liposome preparation and size characterization. Meth. Enzymol. 171, 193-217, 1989.

The invention claimed is:

1. Liposome-like vesicle, or glycerosomes, for pharmaceutical and cosmetic topical application, comprising:
   a) from 20% to 35% w/w glycerol;
   b) from 1% to 10% w/w of at least one phospholipidic component, wherein said phospholipidic component is selected from a group consisting of phosphatidylethanolamine, phosphatidylserine, phosphatidylinositol, dimiristoylphosphatidylcholine, dipalmitoyl phosphatidylcholine, distearoyl phosphatidylcholine, palmitoylstearoyl phosphatidylcholine and sphingomyelin; and
   c) at least one pharmaceutically or cosmetically active principle, wherein said liposome-like vesicles do not contain ethanol.

2. Glycerosomes according to claim 1, containing from 20% to 30% w/w glycerol.

3. Glycerosomes according to claim 1 further containing a modifier of phospholipid membranes in concentration from 0 to 2% w/w and/or an enhancer of cutaneous absorption in concentration from 0 to 5% w/w.

4. Glycerosomes according to claim 3, wherein said modified of phospholipid membranes is selected from a group consisting of cholesterol, stearylamine, dicetylphosphate and phosphatidylglycerol.

5. Glycerosomes according to claim 3, wherein said enhancer of cutaneous absorption is selected from a group consisting of propylene glycol, menthol and fatty acids.

6. Glycerosomes according to claim 1, wherein the pharmaceutical or cosmetic active ingredient is selected from a group consisting of antiviral drugs, vitamins and derived thereof, vegetal extracts, antiinflammatory drugs, corticosteroids, antibiotics, fungicidal drugs, antpsoriasis drugs, acyclovir, trans-retinoic acid, betamethasone and derivatives, lidocaine, minoxidil, amphotericin B, gentamycin, rifampicin, vitamin E and esters or lipophilic derivatives of vitamin E, diclofenac sodium, lidocaine hydrochloride, alkaloids, hydroxyacids, hyaluronic acid, vitamin C and its derivatives, soluble derivatives of vitamin E, vitamin E TPGS, antiwrinkles and antiaging compounds, antioxidants, products for hair treatments, humectants and sunscreen ingredients.

7. A process for the preparation of glycerosomes according to claim 1, comprising mixing 1-10% w/w phospholipidic component, 20-35% w/w glycerol, 0.1-10% w/w pharmaceutically or cosmetically active principle, 0-2% w/w phospholipid membrane modifier; 0-5% w/w cutaneous absorption enhancer and water to 100% and obtaining a colloidal system comprising unilamellar or multilamellar vesicles.

8. A process according to claim 7, carried out at room temperature.

9. A pharmaceutical or cosmetic composition for topical administration comprising the glycerosomes of claim 1.

10. Pharmaceutical or cosmetic composition of claim 9 in the form of a cream, emulsion, ointment, gel, lotion or suspension.

11. Glycerosomes according to claim 1, containing 25% w/w glycerol.

12. Process according to claim 7, carried out at a temperature lower than 30° C.

13. Process according to claim 8, carried out at a temperature of 25° C.

* * * * *